United States Patent [19]
Bannon et al.

[11] Patent Number: 5,135,480
[45] Date of Patent: Aug. 4, 1992

[54] TRANSDERMAL DRUG DELIVERY DEVICE

[75] Inventors: Yvonne B. Bannon, County Kildare; John Corish; Owen I. Corrigan, both of County Dublin; Joseph G. Masterson, Dublin, all of Ireland

[73] Assignee: Elan Transdermal Limited, Athlone, Ireland

[21] Appl. No.: 617,945

[22] Filed: Nov. 21, 1990

Related U.S. Application Data

[63] Continuation of Ser. No. 71,755, Jul. 9, 1987, abandoned.

[30] Foreign Application Priority Data

Jul. 10, 1986 [IE] Ireland ............................... 1854/86

[51] Int. Cl.$^5$ ............................................. A61N 1/30
[52] U.S. Cl. ...................................... 604/20; 128/639; 128/644; 128/799
[58] Field of Search ...................... 128/639–644, 128/635, 798, 799, 802, 803; 604/20

[56] References Cited

U.S. PATENT DOCUMENTS

| | | | |
|---|---|---|---|
| 2,493,155 | 1/1950 | McMillan | 604/20 |
| 4,141,359 | 2/1979 | Jacobson et al. | 604/20 |
| 4,383,529 | 5/1983 | Webster | 604/20 |
| 4,474,570 | 10/1984 | Ariora et al. | 604/20 |
| 4,557,723 | 12/1985 | Sibalis | 604/20 |
| 4,622,031 | 11/1986 | Sibalis | 604/20 |
| 4,640,689 | 2/1987 | Sibalis | 604/20 |
| 4,708,716 | 11/1987 | Sibalis | 128/635 |
| 4,731,049 | 3/1988 | Parsi | 604/20 |

FOREIGN PATENT DOCUMENTS

| | | |
|---|---|---|
| 0058920 | 2/1982 | European Pat. Off. |
| 0060451 | 3/1982 | European Pat. Off. |
| 2104388A | 7/1982 | United Kingdom |

OTHER PUBLICATIONS

J. P. Astlet, et al., "Effect of Dimethyl Sulfoxide on Permeability of Human Skin In Vitro", 65 J. Pharm Sci. 210 (1976).
R. B. Toughton, et al., "Azone: A New Non-toxic Enhancer of Cutaneous Penetration", 9 Drug Development and Industrial Pharmacy 725 (1983).
Y. W. Chien, "Comparative Controlled Skin Permeation of Nitroglycerin from Marketed Transdermal Delivery Systems", 72 (8) J. Pharm. Sci. 968 (1983).
J. F. Dasta, et al. "A New Twist on an Old Standby", 2 American Pharm. (1982).
J. E. Shaw, et al. "Percutaneous Absorption: Controlled Drug Delivery For Topical or Systemic Therapy", 67 J. Invest. Dermatol. 677 (1976).
C. R. Behl, et al., "Hydration and Percutaneous Absorption IV: Influence of Hydration on n-Alkanol Permeation Through Rat Skin; Comparison With Hairless and Swiss Mice", 72 (1) J. Pharm. Sci. 79 (1983).
B. J. Idson, "Percutaneous Absorption", 64 Pharm. Sci. 901 (1975).
A. S. Michaels, et al., "Drug Permeation Through Human Skin: Theory and in Vitro Experimental Measurement", 21 A.I. Ch. E. 985 (1975).
J. Swarbrick, et al. "Drug Permeation Through Human Skin II: Permeability of Ionizable Compounds", 73 J. Pharm. Sci. 1352 (1984).
J. L. Zatz, "Fundamental of Transdermal Controlled Drug Administration: Physicochemical Considerations", 9 Drug. Dev. Ind. Pharm. 561 (1983).

(List continued on next page.)

Primary Examiner—Lee S. Cohen
Assistant Examiner—J. P. Lacyk
Attorney, Agent, or Firm—Marla J. Church

[57] ABSTRACT

A transdermal device having a detachably mounted electrode with a first surface adapted for contact with human skin and through which a drug substance contained in the electrode passes to the skin under the influence of an iontophoretic or electro-osmotic force and a second surface which is electrically conducting, the electrode has a surface area in contact with the skin, in use, in the range 0.1 to 30 cm$^2$ and a drug dissolved or dispersed in a hydrophilic medium at a concentration in the range 0.1 to 15% (w/v) based on the hydrophilic medium.

16 Claims, 7 Drawing Sheets

OTHER PUBLICATIONS

J. Hadgraft, "Theoretical Aspects of Metabolism in the Epidermis" 4 Int. J. Pharm. 229 (1980).

R. H. Guy, et al. "Percutaneous Metabolism With Saturable Enzyme Kinetics", 11 Int. J. Pharm. 187 (1982).

D. C. Boone, "Clinics in Physical Therapy: Electrotherapy", Ed. Wolf, S. L. Ch. 5, p. 99.

L. W. Gibson, et al. "A Test For Concentration of Electrolytes in Sweat in Cystic Fibrosis of the Pancreas Utilizing Pilocarpine by Iontophoresis", 23 Pediatrics 545 (1959).

M. W. M. Bridger, et al. "A Device For Iontophoretic Anaesthesia of the Tympanic Membrane", 6 J. Med. Eng. Tech. 62 (1982).

R. T. Ransden, "Anaesthesia of the Tympanic Membrane Using Iontophoresis" 91 J. Larynoglogy & Otology 779 (1977).

Johnson, et al. "The Patency of Sweat Ducts in Normal-Looking Skin" 83 British J. Dermatol. 367 (1970).

O. Siddiqui, et al. "The Effect of Iontophoresis and Vehicle pH on the In-Vitro Permeation of Lignocaine Through Human Stratum Corneum" 37 J. Pharm, Pharmacol. 732 (1985).

L. P. Gargarosa, et al. "Conductivity of Drugs Used for Iontophoresis" 67 J. Pharm. Sci. 1439 (1978).

T. J. Franz "Percutaneous Absorption of the Relevance of In Vitro Data" 64 J. Invest, Dermatol. 190 (1975).

A. M. Klingman, et al. "Preparation of Isolated Sheets of Human Stratum Corneum", vol. 88, Archives Dermatol. 702 (1963).

TRANSDERMAL DRUG DELIVERY DEVICE

This is a continuation of copending application Ser. No. 07/071,755 filed on Jul. 9, 1987 now abandoned.

BACKGROUND OF THE INVENTION

This invention relates to a device for the transdermal delivery of drugs and, in particular, to an electrode for use in a transdermal device which includes means for assisting or enhancing and controlling drug transport to the systemic circulation.

DESCRIPTION OF THE PRIOR ART

The study of the penetration of drugs through the skin has become increasingly important in recent years. The aims of such enhanced and controlled delivery are to maximize the bioavailability of the drug, to optimize the therapeutic efficacy and to minimize side effects.

There are many potential advantages of the transdermal route over the more conventional methods of drug administration. These advantages may be summarized in the following way.

Transdermal administration means that the drug may be introduced into the systemic circulation without initially entering the portal circulation where it may be metabolized into a pharmacologically inactive form (first pass effect). For drugs that are normally taken orally, administration through the skin can eliminate factors such as pH changes and food intake that influence gastrointestinal absorption. One of the most important advantages of the transdermal route is that it provides constant and continuous absorption of the drug, thus keeping blood levels within the "therapeutic window". In contrast, oral administration is often associated with variable absorption with blood levels sometimes rising to toxic levels or falling to subtherapeutic levels. The transdermal route is, therefore, a suitable route for the administration of very potent drugs, drugs with short half lives and low therapeutic indices or drugs which are subject to significant first pass effects.

Transdermal administration may allow rapid termination of drug input should side effects occur, and it increases patient compliance. The route is, however, clearly not suitable for drugs that seriously irritate or sensitize the skin, and for passive administration is restricted to drugs of suitable molecular configuration.

Many of the drugs that are otherwise suitable for transdermal delivery do not achieve sufficiently high blood levels for pharmacological activity when administered transdermally so that it is sometimes necessary to enhance this delivery. This can be achieved by chemical means namely by the use of absorption promoters e.g. aprotic solvents such as dimethylsulfoxide (DMSO), Azone (Trade Mark) and surfactants (Astley and Levine (1976) J. Pharm. Sci. 65, 210–215; Stoughton and McClure Drug Dev. Ind. Pharm. (1983) 9, 725–744).

In order that a transdermal delivery device may control the rate of penetration of the drug through the skin, it must release the drug at a rate which is less than that at which it can permeate the skin. Under these conditions, the more readily the drug is released from the drug delivery system, the higher the rate of transdermal absorption. The rate of drug release depends on whether the drug molecules are suspended or dissolved in the vehicle and on the interfacial partition coefficient of the drug between the delivery system and the skin.

A number of transdermal drug delivery systems have been developed and are currently in use. The drugs incorporated into these systems include nitroglycerin, which has been used for the treatment and prevention of angina pectoris, scopolamine for the treatment of motion sickness, the antihypertensive, clonidine and steroid hormones such as estradiol. These devices typically contain the active constituent dispersed or suspended in a reservoir: its rate of release is controlled either by matrix diffusion or by its passage through a controlling membrane.

The release characteristics of a number of these commercially available passive systems have been investigated by many researchers, including Chien, Y. W. (1983) J. Pharm. Sci. 72, 968–70, Dasta, J. F. and Gerates, D. R. (1982) and Shaw, J. E., et al (1976) J. Invest. Dermatol. 67, 677–678. Many other drugs are at present being evaluated for their suitability for transdermal administration.

The skin consists of three distinct layers; the epidermis, the dermis and subcutaneous fat. The outermost layer of the epidermis, the stratum corneum, is generally accepted to be the rate limiting barrier to drug penetration.

Hydration is one of the most important factors in skin penetration and may increase the absorption of substances that penetrate the skin Behl, C. R. et al (1983) J. Pharm. Sci., 72, 79–82. Hydration results from water used in the preparation of the transdermal device.

The mobility of water molecules per se within the hydrated stratum corneum is crucial to the permeability of water soluble substances because they are very probably dissolved within this absorbed water. Just as diffusion in dilute aqueous solution requires cooperative motion of water molecules, the permeability of water-soluble substances through the stratum corneum likewise, depends on the mobility of water molecules surrounding the solute, Idson, B. J. (1975) Pharm. Sci., 64, 901–924.

The rate of percutaneous absorption can be affected by the oil/water partition coefficient, the polarity of the drug and its degree of ionization, its solubility characteristics, molecular weight, volatility, concentration and the nature of the drug vehicle.

Many compounds evaluated for their ability to undergo percutaneous absorption are strong to weak electrolytes. Depending on the $pK_a$ of the drug and the pH of the vehicle, such compounds exist in an equilibrium mixture of ionized and unionized species. To properly control the rate at which such electrolytes permeate the skin, it is necessary to determine the permeability coefficients of both forms of the drug. Michaels, A. S. et al (1975) A. I. Ch.E. 21, 985–996, calculated the permeabilities of the ionized forms of scopolamine and ephedrine to be 1/20th of those for the unionized forms. The permeation of the ionized drug through the skin is therefore possible and cannot be assumed to be negligible especially at pH levels at which large concentrations of ionized molecules are present, i.e., substances with low $pK_a$ values, Swarbrick, J. et al (1984) J. Pharm. Sci., 73, 1352–1355.

Other factors that affect the rate of absorption of drugs across the skin include chemical effects such as binding of the drug in the epidermis, (Zatz, J. L. (1983) Drug. Dev. Ind. Pharm., 9, 561–577 and the metabolism of the drug as it penetrates the skin, (Hadgraft, J. (1980) Int. J. Pharm., 4, 229–239, Guy, R. H. and Hadgraft J. (1982) Int. J. Pharm., 11, 187–197. The rate of percutaneous absorption is influenced by the temperature and increases as the temperature is raised. An increase in temperature may be effected by occluding the absorption site or by application of an absorption enhancer such as DMSO or a surfactant.

Anatomical differences in penetration rates seem to depend largely on the thickness of the stratum corneum, with rates increasing in the following anatomical order: plantar; anterior forearm; instep; scalp; scrotum; and posterior auricular.

The technique of iontophoresis has been used on a limited scale in medical therapy. Iontophoresis is the process of moving ions into surface tissues with the aid of an electrical current, Boone, D. C. (1982) in "Clinics in Physical Therapy: Electrotherapy", Ed. Wolf, S. L., Ch. 5, p 99-121. The technique was discovered nearly a century ago, but it is only in recent years that much interest has been shown in it as a method of local drug administration of ions; its chief proponents are to be found in the disciplines of dermatology, dentistry and otolaryngology. It is a safe, well documented method of introducing ions or polar substances into the skin by the application of a direct current between two electrodes placed on the skin of the patient e.g. pilocarpine, local anaesthetics, anti-virals (Gibson, L. W. and Cooke R. E. (1959) Pediatrics, 23, 545-549; Bridger M. W. M. et al, (1982) J. Med. Eng. Tech., 6, 62-64; Ramsden R. T. (1977) J. Laryngology and Otology., 91, 779-785; Johnson, C. and Shuster, S. (1970) British J. Dermatol., 83, 367-379; Siddiqui, 0. et al (1985) J. Pharm. Pharmacol., 37, 732-735. One advantage claimed for iontophoresis as a technique for drug administration is that systemic toxicity is virtually eliminated, since only a small amount of drug is delivered. (Gangarosa L. P. et al (1978) J. Pharm. Sci., 67, 1439-1443).

Transdermal devices are known from Patent Publication GB 2 104 388A and also from U.S. Pat. Nos. 4,557,723, 4,622,031 and 4,640,689. However, all of the devices disclosed in the aforementioned four documents are applied to the skin by adhesive means. The use of adhesive at the site of application of a drug which is to be administered by the transdermal route can cause severe irritation which may necessitate discontinuing such transdermal treatment. The irritation observed is frequently far more severe than the irritation caused by the drug itself which is sometimes observed at the site of application of a transdermal device.

It is an object of the present invention to provide an electrode for use in a transdermal device wherein the transport of drugs from a reservoir for the drug, integral with the electrode, to the skin and thence to the systemic circulation is promoted and controlled by means integral with the device and capable of supplying an electric current as a driving force for said drug transport.

It is a further object of the invention to provide a transdermal device which is portable and easy to operate and which can be readily adapted to meet the special requirements particular to a given drug.

SUMMARY OF THE INVENTION

Accordingly, the invention provides an electrode for use in a transdermal device, said electrode comprising a first surface adapted for contact with human skin and through which a drug substance contained in the electrode may pass to the skin under the influence of an iontophoretic or electro-osmotic force and a second surface remote from said skin-contacting surface which is electrically conducting and which is adapted for contact with an electrical source in said transdermal device, said electrode having a surface area in contact with the skin, in use, which is in the range 0.1-30 $cm_2$, said drug being dissolved or dispersed in a hydrophilic medium in said electrode and said drug concentration being in the range 0.1 to 15% (w/v) based on the hydrophilic medium, and said second surface of said electrode being drug impermeable.

DETAILED DESCRIPTION OF THE INVENTION

Preferably, the hydrophilic medium is a gel material which is formed into a disc, one major surface of said disc defining said skin-contacting surface of said electrode and said other major surface of said disc having an electrically conducting material adhered thereto and defining said second surface of said electrode.

The disc of hydrophilic gel material may have a drug permeable membrane attached to said one major surface and defining said skin-contacting surface of said electrode and a layer of aluminium or platinum foil attached to said other major surface and defining said second surface of said electrode.

Preferably, the hydrophilic medium is a biocompatible polymer or polymeric gel of suitable rigidity and conductance and having the drug distributed therethrough. A wide range of natural and/or synthetic polymeric materials or gelling agents or mixtures thereof may be used to form the hydrophilic medium of the transdermal device according to the invention. Such materials include agar gel, karaya gum gel, polyoxyethylene-polyoxypropylenes such as Pluronic F68 (Pluronic F68 is a Trade Mark) and Pluronic F127 (Pluronic F127 is a Trade Mark), gelatin, sodium carboxymethylcellulose, poly(ethylene oxide) polymers such as Macrogol (Macrogol is a Trade Mark), methylcellulose, carboxyvinyl polymers crosslinked with allyl sucrose such as Carbopol (Carbopol is a Trade Mark) and polyacrylamide gels or mixtures thereof. The term "agar" is synonymous with "agar-agar". The gelling agents may be based on aqueous solvents and co-solvents. The co-solvents include, for example, alcohols such as ethanol, polyols such as glycerol, ethylene glycol and propylene glycol, dimethylformamide, dimethylsulfoxide and other aqueous miscible co-solvents. The reservoir may also include suitable antimicrobial, antifungal and other pharmaceutical excipients secundum artem.

Suitable antimicrobial and antifungal agents/preservatives include benzalkonium chloride, cetrimide (cetyltrimethylammonium bromide), benzoic acid, benzyl alcohol, Parabens (Trade Mark for the methyl-, ethyl-, propyl- and butyl- esters of para-hydroxybenzoic acid), chlorhexidine, chlorobutanol, phenylmercuric acetate, borate and nitrate, potassium sorbate, sodium benzoate, sorbic acid and thiomersal (mercurithiosalicylate) or a mixture thereof.

The hydrophilic medium may also include an anti-oxidant. Preferred anti-oxidants include sodium metabisulphite, butylated hydroxyanisole and butylated hydroxytoluene or a mixture thereof.

The hydrophilic medium may also include a pH-controlling agent. Preferred pH-controlling agents include citric acid and sodium citrate.

The hydrophilic medium may also include a plasticizer. Suitable plasticizers include diethylphthalate, dibutylphthalate and tributylcitrate or a mixture thereof.

The hydrophilic medium may also include a surfactant. Suitable surfactants include sodium lauryl sulphate, diethylene glycol monostearate, propylene glycol monostearate, polyethylene glycols as sold under the Trade Mark MACROGOL, polysorbates and polyvinyl alcohol or a mixture thereof.

The hydrophilic medium may also include a penetration enhancer. Suitable penetration enhancers include dimethylsulfoxide, N,N-dimethylacetamide, N,N-dimethylformamide, 2-pyrrolidone, N-methyl-2-pyrrolidone and 1-dodecyl azacyclo-heptan-2-one or a mixture thereof.

The hydrophilic medium may also include a humectant. A particularly preferred humectant is glycerol for use in a high humidity environment.

Further the hydrophilic medium may also include a local anaesthetic. Suitable local anaesthetics include lidocaine, benzocaine, lignocaine, methocaine, butylaminobenzoate and procaine or a mixture thereof. The preparation would include a local anaesthetic mainly to suppress irritation at the site of application thereof caused by the drug.

Additionally, the hydrophilic medium may include a rubefacient. Particularly preferred rubefacients include camphor and menthol or a mixture thereof and other locally acting peripheral vasodilators.

The electrode according to the invention will normally have a contact area less than 10 $cm^2$.

In addition to the electrical source the essential components of the electrical circuit including the electrode hereinafter referred to also as said first electrode, are a means of adjusting the current, a means of indicating the successful operation of the device, i.e. an indicator light to show that the current is in the required range for the correct administration of the particular drug and a second electrode, which may be a counter electrode, which in use will be situated at a different site on the skin to said first electrode. The counter electrode will comprise a suitable metal or polymer such as a conductive resin or rubber and may contain a suitable conducting gel and/or an adhesive. The second electrode may also comprise an electrode of the type defined for said first electrode. Accordingly, the device incorporating the electrode according to the invention may be used to administer two drugs simultaneously by the transdermal route. When it is desired to administer two drugs of opposite charge, the first and second electrodes must be housed in chambers of opposite polarity.

More especially, the first electrode and the electrical source will be housed in a single unit which may also preferably include an LCD (liquid crystal display) and a control circuit. The LCD may display current, voltage and timing readings, as required. The exterior surface of the unit will, therefore, simulate the face of a time piece. The unit may include an ammeter and preferably a voltage adjuster. The control circuit may also include a galvanostat which regulates the current and maintains the current constant despite varying resistance of the skin. The power supply will suitably comprise conventional miniature or "light-weight" batteries. For example, conventional sheet batteries and microbatteries may be used.

The unit may also include a timing circuit which will activate the device at selected intervals or give a signal in the form of a bleep which will prompt the user to activate the device at selected intervals of time. However, the device can also be used for continuous administration of a drug and for continuous assisted drug transport.

The current used can be in the region of 0.01-10 mA. For example, the device can suitably operate at 0.5 mA at 10-20 volts. The current may be constant, variable or pulsed.

In a particularly preferred embodiment, the transdermal device includes a support means for attaching the device to a limb or appendage of the body. Such a support means is suitably in the form of a strap or bracelet, more particularly a wrist watch strap or bracelet. In place of a strap one may use a hollow bracelet. When a hollow bracelet is used the lead from the power supply to the counter electrode would be housed in the interior of the bracelet.

The second or counter electrode may be located in the bracelet or strap at a point distant from the first electrode or, alternatively, the two electrodes may be located adjacent to one another but separated by an insulating material.

The term "drug" as used herein embraces most pharmacologically active substances and also nutritional supplements such as vitamins and electrolytes. Especially suitable pharmacologically active substances for use as the drug in the electrode according to the invention include, for example, clonidine or a salt thereof, insulin, morphine, nicotine, orcipreniline or a salt thereof, salbutamol or a salt thereof, sodium chromoglycate and the peptide desmopressin. It will be appreciated that many drugs are actually administered in the form of a pharmaceutically acceptable salt.

As indicated above the device incorporating the electrode according to the invention may be used to administer two drugs simultaneously by the transdermal route. An example of drugs which may be suitably administered in this way are a combination of orcipreniline sulphate or salbutamol and sodium chromoglycate in the treatment of asthma.

Suitable concentrations for the preferred drugs for use in the electrode according to the invention are:

nicotine 0.2-5% (w/v) based on the hydrophilic medium;

clonidine 2-8% (w/v) based on the hydrophilic medium;

salbutamol 1-6% (w/v) based on the hydrophilic medium;

morphine 0.4-8% (w/v) based on the hydrophilic medium;

orcipreniline 0.1-20% (w/v) based on the hydrophilic medium;

sodium chromoglycate 1-10% (w/v) based on the hydrophilic medium;

desmopressin 0.1-5% (w/v) based on the hydrophilic medium; and insulin 0.1-1% (w/v) based on the hydrophilic medium.

A particular advantage of the present transdermal device is that the electrode incorporating the drug reservoir defined by said hydrophilic medium forms an integral unit which can be discarded once the drug supply is used up. Hence one does not experience the problem which is characteristic of certain conventional transdermal devices which are used in association with an electrode and wherein the drug reservoir only is disposable. With such devices residues of material defining the drug reservoir adhere to the electrode when the drug supply of the reservoir is exhausted. Such residues build up with time, such that the device becomes progressively less effective and it becomes increasingly difficult to transport the drug to the skin surface in use.

The hydrophilic gel medium used in the electrode according to the invention is biocompatible, stable, easy to handle and compatible with the conducting material of the electrode.

BRIEF DESCRIPTION OF THE DRAWINGS

The invention will be understood from the following description of an embodiment thereof given by way of example only with reference to the accompanying drawings in which:

FIG. 2 is a circuit diagram of the circuit employed in the transdermal device depicted in FIG. 1a;

Referring to FIG. 1a of the drawings, there is indicated generally at 1 a transdermal device incorporating a disposable electrode 3 according to the invention, said device 1 comprising a housing 2 for the electrode 3 (FIG. 1b) which consists of an electrically conducting layer 4 and a disc of 4% agar gel 5 in which is dispersed salbutamol at a concentration of 27.5 mg/ml and which is attached to the site of application by means of a strap 6 having at the free ends thereof the cooperating elements of a conventional clasp 7. The electrode 3 is connected by a lead 8 to a source of electrical potential comprising a power supply 9, a control and timing circuit 10, an ammeter 11, a galvanostat 12 and a fixed metal electrode 13 against which is placed the conducting layer 4 of the electrode 3.

Figure 1A:
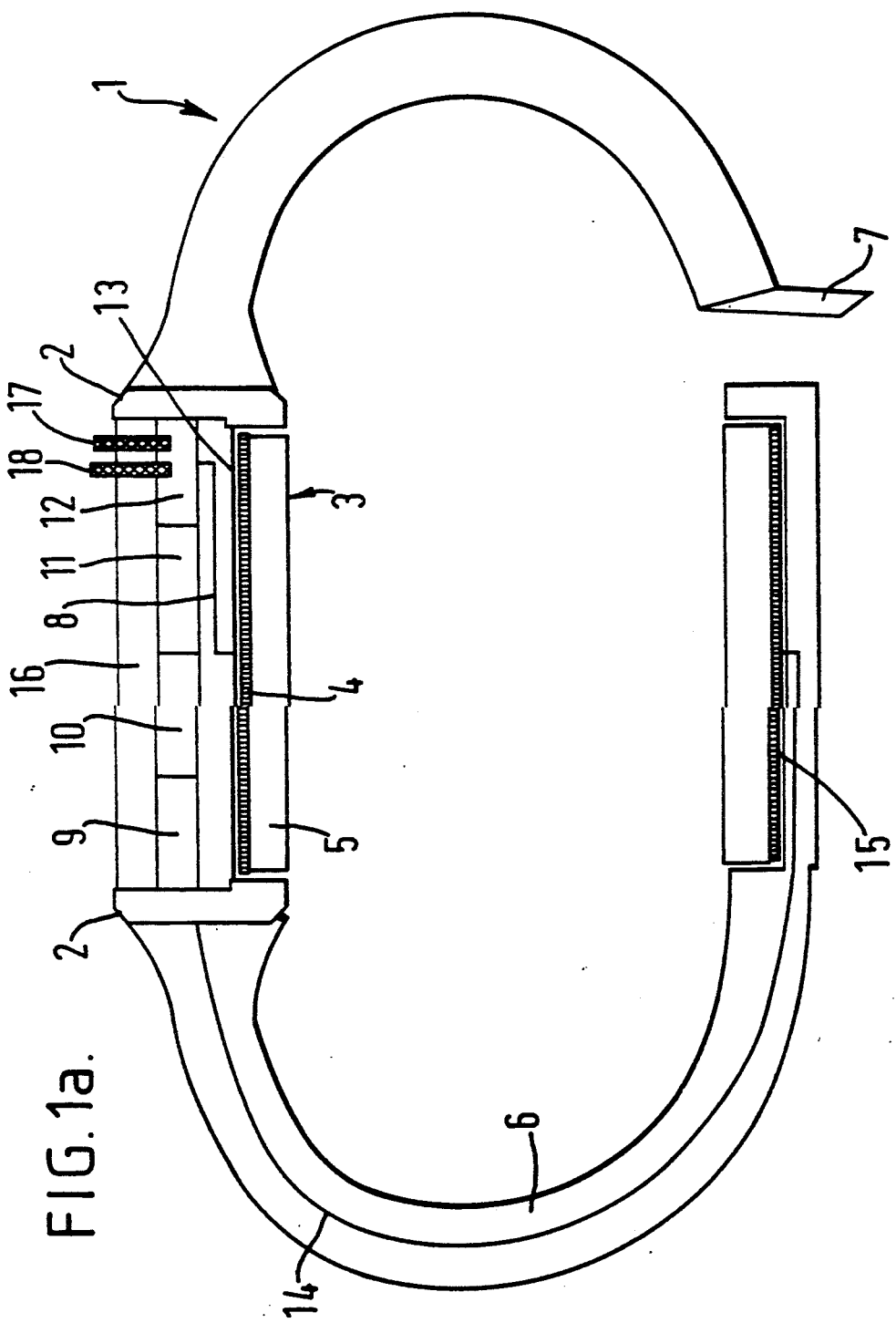
FIG. 1a is a schematic representation of a transdermal device incorporating an electrode according to the invention.
Figure 1B:
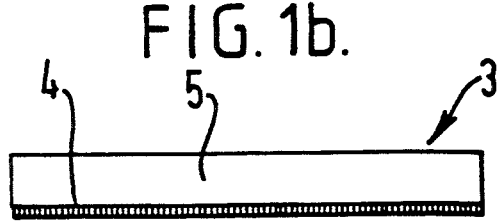
FIG. 1b is a schematic representation of the electrode according to the invention.

The power supply 9 is also connected via a lead 14 to a counter electrode 15 located adjacent the clasp 7 and which electrode 15, in use, allows the circuit to be completed when the device is applied to the skin. The electrode 15 comprises a layer of a conducting gel, one major surface thereof defining a skin-contacting surface and the other major surface thereof having intimately associated thereto a metallic conducting layer. The power supply 9 comprises two minature batteries (2.5 V). The device 1 also contains an LCD 16 with appropriate switching arrangements which can display time, current and voltage, an audible alarm/warning device which prompts the user to activate the device by pressing an on/off button 17, and an LED (light emitting diode) to indicate satisfactory operation of the device.

Figure 2:
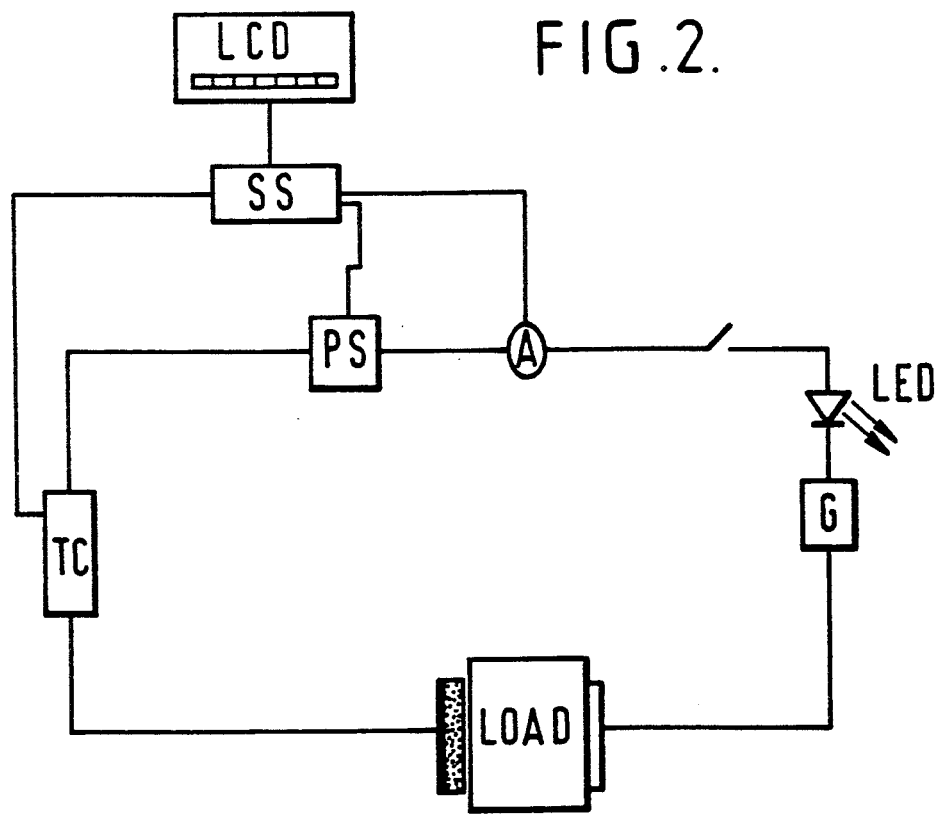

The main components of the circuit employed in the device 1 are depicted in the circuit diagram comprising FIG. 2. Said components are as follows:

TC — a timing circuit, optionally programmable and with an audible warning device;

PS — a power supply with reversible polarity;
A — an ammeter;
G — a galvanostat;
SS — a selective switch;
LCD — a liquid crystal display for time, voltage or current, as selected;
LED — a visible signal of satisfactory operation of the device.

The invention will be further illustrated by the following Examples.

EXAMPLE 1

A nicotine-containing agar gel was prepared by dispersing 4% agar in glycerol:water (1:4) and dissolving nicotine (98–100% anhyd.;Sigma Chemicals N3876) therein so as to achieve a concentration of 55 mg/ml. While still in the liquid state, the gel so prepared was spread on a layer of aluminium foil so as to obtain an electrode according to the invention having a surface area of 8 cm$^2$.

Figure 3:
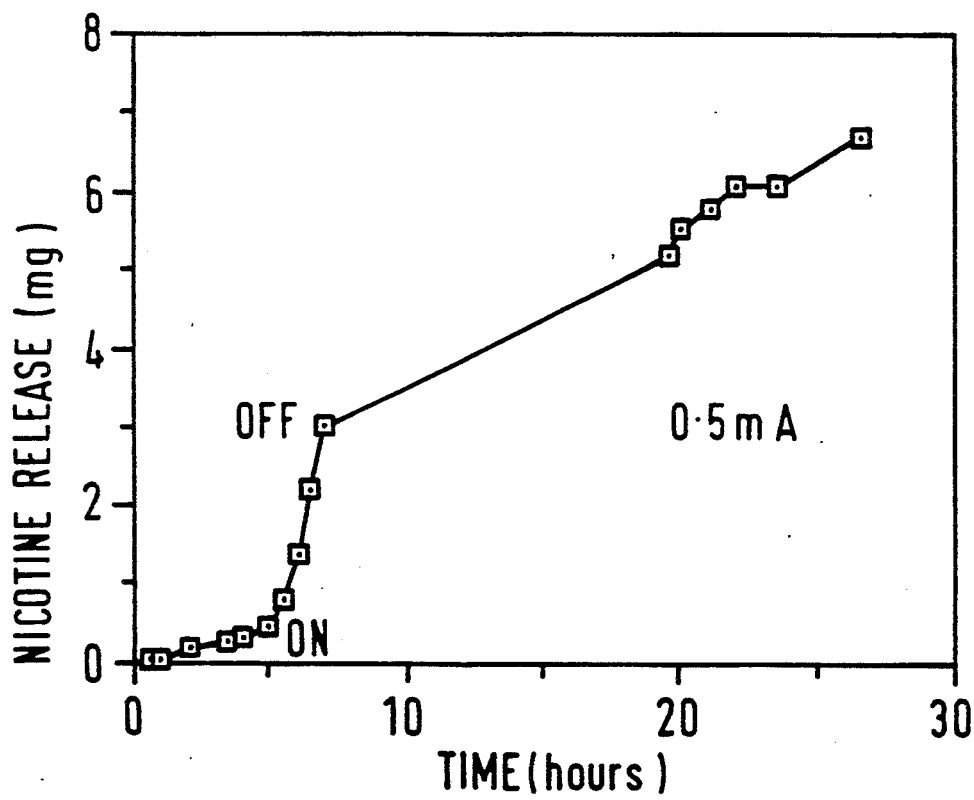
FIG. 3 is a plot of in vitro nicotine release (mg) versus time (hours) for the electrode as prepared in Example 1.

In vitro release of nicotine from the electrode so prepared was determined in a glass, custom built diffusion cell based on the Franz cell (Franz T. J. (1975) J. Invest. Dermatol., 64, 190). Full thickness abdominal skin (approx. 4 cm×15 cm) taken from cadavers within 48 hours post mortem was used in the in vitro characterisation as the transport membrane. The stratum corneum and epidermis (SCE) were separated from the other skin layers using the method of A. M. Kligman and E. Christophers (Archives Dermatology (1963) Vol. 88, pages 702–705). The nicotine transported through the membrane was analysed using a Pye Unicam SP 200 (Trade Mark) uv/vis spectrophotometer and by reverse phase HPLC. The nicotine release is depicted in FIG. 3 of the accompanying drawings.

EXAMPLE 2

Figure 4:
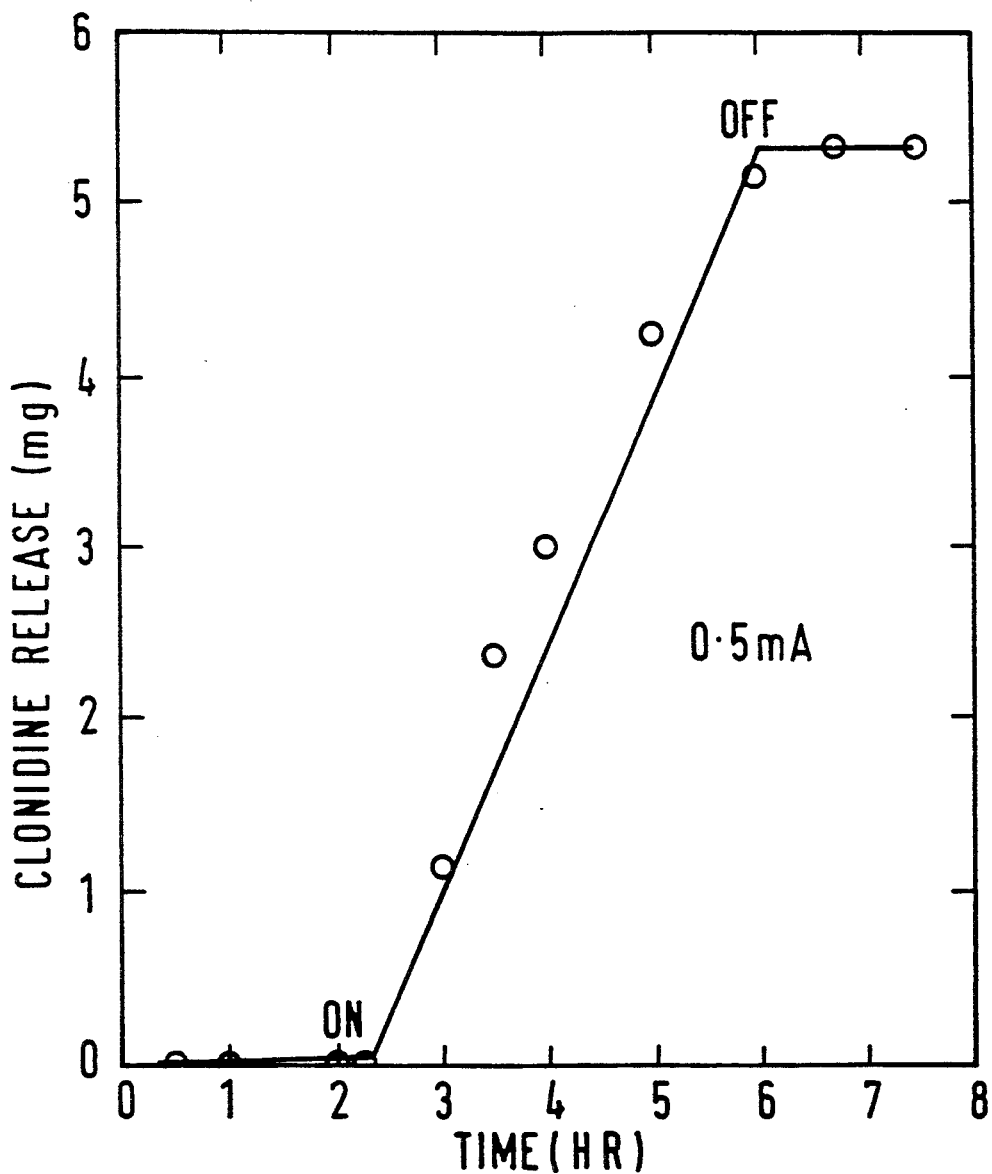
FIG. 4 is a plot of in vitro clonidine release (mg) versus time (hours) for the electrode as prepared in Example 2.

Example 1 was repeated except that nicotine was replaced by clonidine hydrochloride and the clonidine hydrochloride was dissolved in 4% agar gel so as to achieve a concentration of clonidine hydrochloride of 27 mg/ml. The in vitro release of clonidine was measured according to the procedure of Example 1 and the release is depicted in FIG. 4 of the accompanying drawings.

EXAMPLE 3

Figure 5:
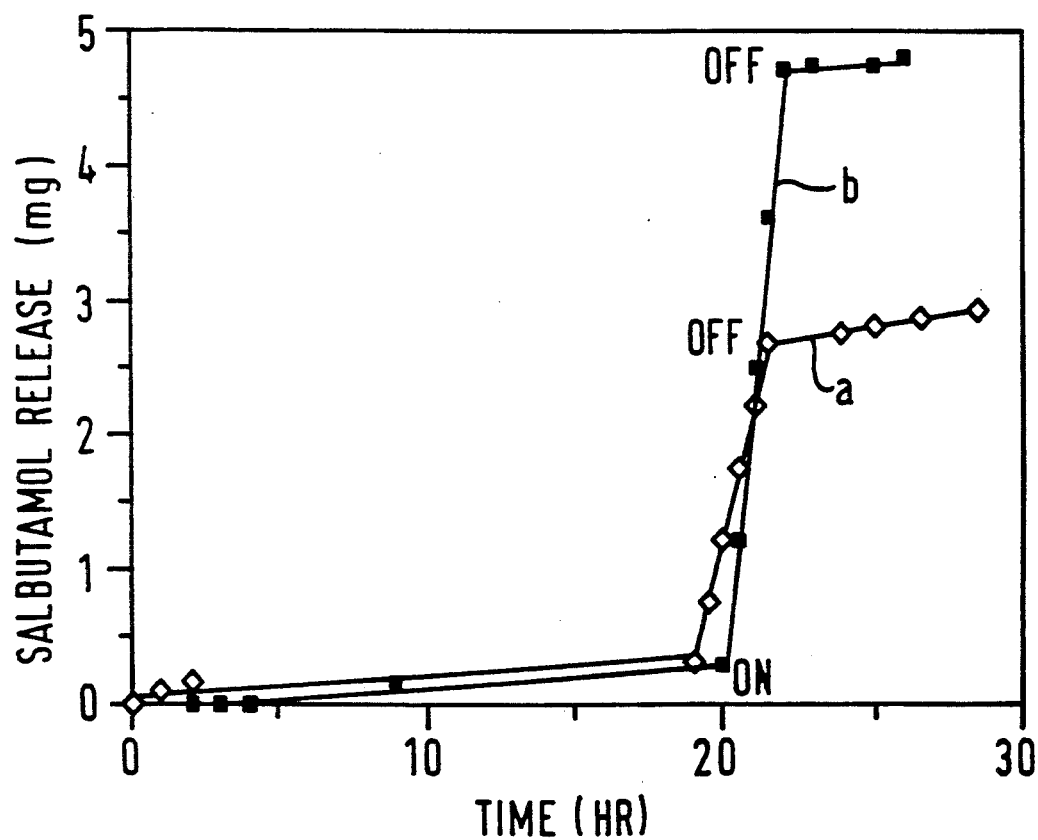
FIG. 5 is a plot of in vitro salbutamol release (mg) versus time (hours) at 0.25 mA (curve a) and 0.5 mA (curve b) for the electrode as prepared in Example 3.

Example 1 was repeated except that nicotine was replaced by salbutamol and the salbutamol was dissolved in a gel made from methylcellulose (0.16%) and agar (3.84%) so as to achieve a concentration of salbutamol of 27.5 mg/ml. The in vitro release was measured according to the procedure of Example 1 and the release is depicted in FIG. 5 of the accompanying drawings.

Figure 6:
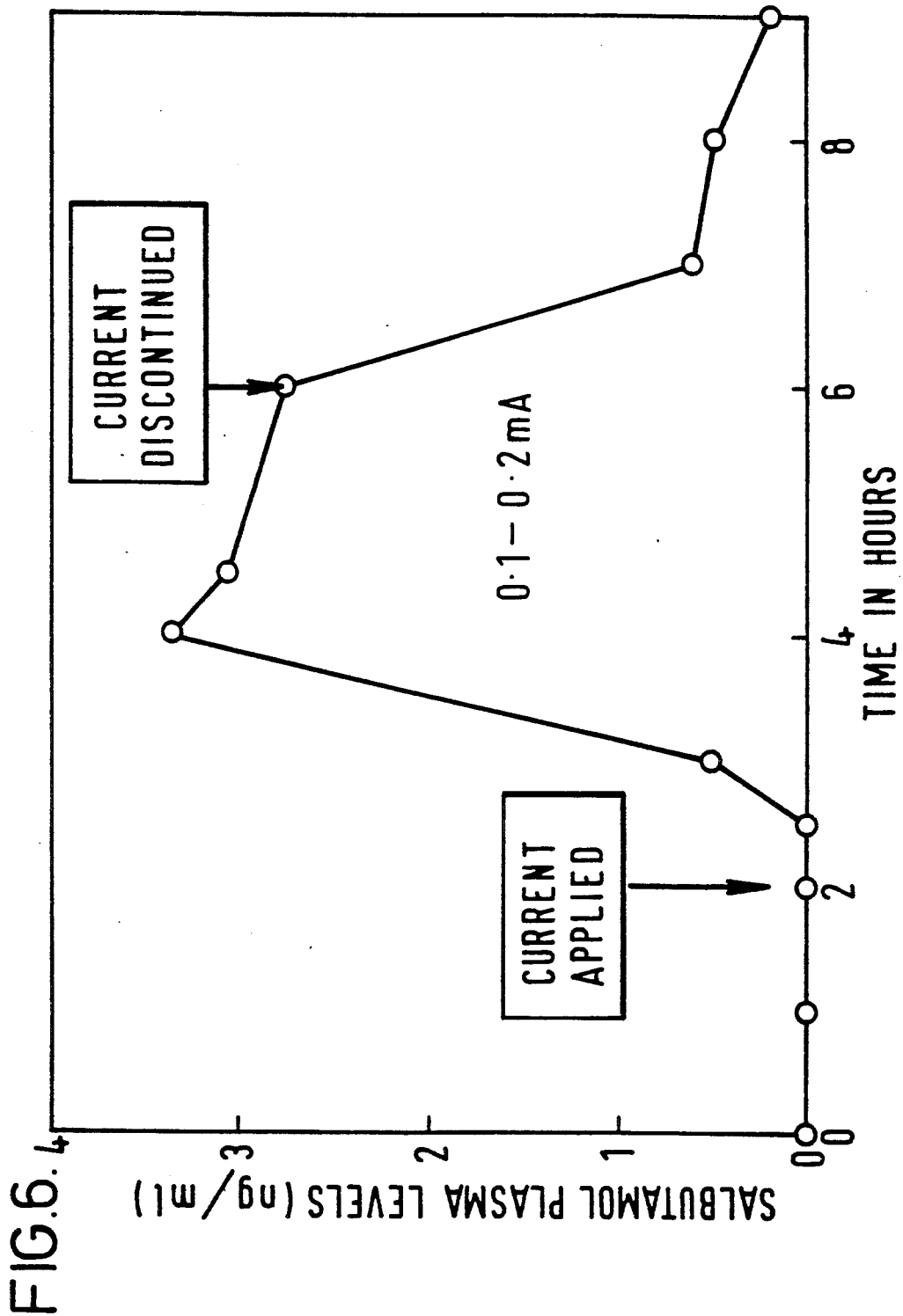
FIG. 6 is a plot of in vivo salbutamol plasma levels (ng/ml) versus time (hours) for the electrode as prepared in Example 3.

The release of salbutamol from the electrode so prepared was also measured in vivo in two subjects and the mean results are depicted in FIG. 6 of the accompanying drawings.

EXAMPLE 4

Figure 7:
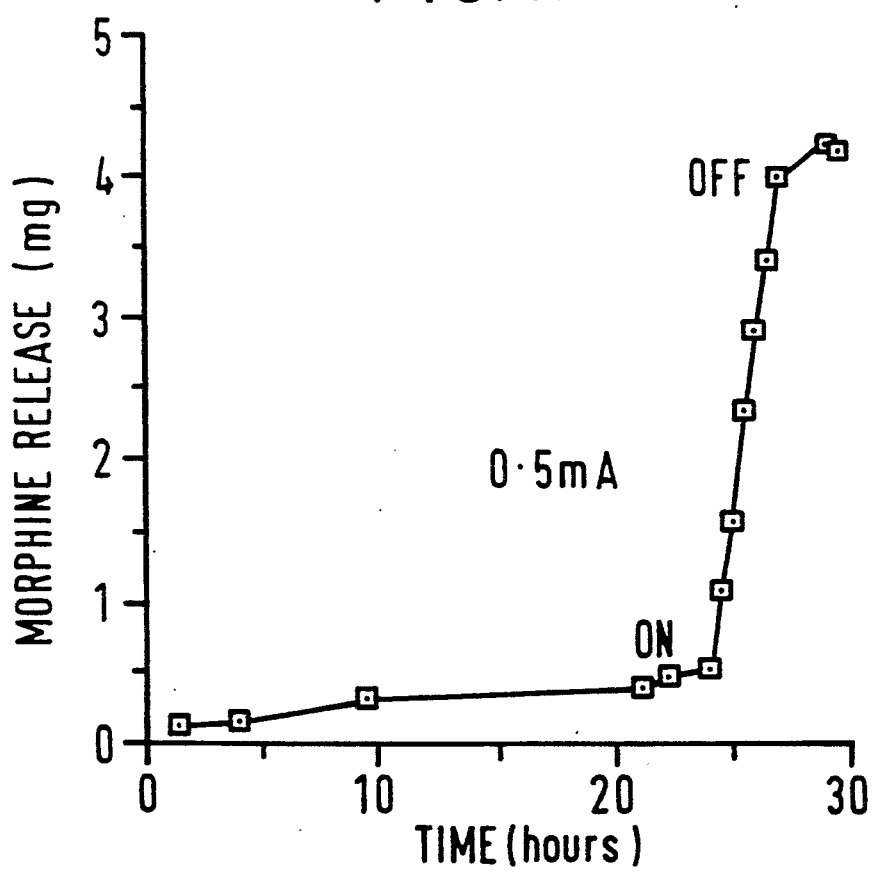
FIG. 7 is a plot of in vitro morphine release (mg) versus time (hours) for the electrode as prepared in Example 4.

Example 1 was repeated except that nicotine was replaced by morphine and the morphine was dissolved in 5% agar gel so as to achieve a concentration of 55 mg/ml. The in vitro release was measured according to the procedure of Example 1 and the release is depicted in FIG. 7 of the accompanying drawings.

EXAMPLE 5

Example 1 was repeated except that nicotine replaced by desmopressin and the desmopressin was dissolved in a gel made from karaya gum (30%) so as to achieve a concentration of desmopressin of 3 mg/ml.

EXAMPLE 6

Example 1 was repeated except that nicotine was replaced by insulin and the insulin was solubilized in a 30% aqueous gel containing polyacrylamide (approx. $15 \times 10^6$ molecular weight) so as to obtain a concentration of insulin of 4 mg/ml.

EXAMPLE 7

Separate electrodes containing sodium chromoglycate and salbutamol, respectively, were prepared for use in a transdermal device for the simultaneous administration of said drugs by the transdermal route. The sodium chromoglycate electrode was prepared according to the procedure of Example 1 except that nicotine was replaced by sodium chromoglycate and the sodium chromoglycate was dissolved in 4% agar gel so as to achieve a concentration of 30 mg/ml. The salbutamol electrode was prepared in accordance with Example 3 and contained a concentration of salbutamol of 27.5 mg/ml.

What we claim is:

1. A transdermal device suitable for long term administration of a drug substance comprising: a housing; a complete electrical circuit having a first electrode detachably mounted within a recess in said housing, said first electrode having a first surface adapted for contact with human skin and through which the drug substance contained in the first electrode may pass to the skin under the influence of an iontophoretic or electroosmotic force and a second surface remote from said skin-contacting surface which is electrically conducting and which is adapted for contact with an electrical source in said housing such that the first electrode can be discarded and replaced by a new electrode when the drug supply substance is exhausted, said first electrode having a surface area adapted to be in contact with the skin when in use, said drug substance being dissolved or dispersed in a hydrophilic medium defining said first electrode, and said second surface of said first electrode is drug impermeable, a means for adjusting the current, means for indicating the current is in the required range for correct administration, and a second electrode which is optionally detachable for completing said electrical circuit; and a non-adhesive means for securing said device to the skin.

2. A transdermal device according to claim 1, wherein the hydrophilic medium is a gel material which is formed into a disc, one major surface of said disc defining said skin-contacting surface of said first electrode and a second major surface of said disc having an electrically conducting material adhered thereto and defining said second surface of said first electrode.

3. A transdermal device according to claim 2, wherein the disc of hydrophilic gel material has a drug permeable membrane attached to said one major surface and defining said skin-contacting surface of said first electrode and a layer of aluminium or platinum foil attached to said second major surface and defining said second surface of said first electrode.

4. A transdermal device according to claim 3, wherein the hydrophilic medium is selected from the group consisting of agar gel, karaya gum gel, a polyoxyethylene-polyoxypropylene gel, gelatin, sodium carboxymethylcellulose, a poly(ethylene oxide) polymer, methylcellulose, carboxyvinyl polymers cross linked with allyl sucrose and polyacrylamide gels or a mixture thereof.

5. A transdermal according to claim 1, wherein the hydrophilic medium contains one or more additional agents selected from the group consisting of antimicrobial agents, antifungal agents, preservatives, anti-oxidants, pH-controlling agents, plasticizers, surfactants, penetration enhancers, humectants, local anaesthetics and rubefacients.

6. A transdermal device according to claim 1, wherein the second electrode connected to said housing such that, when in use, will be situated is a different site on the skin to said first electrode.

7. A transdermal device according to claim 6, wherein the components of the electrical circuit, excluding the second electrode, are housed in a single unit, the exterior surface of said unit simulating the face of a time piece, said unit being mounted in a strap or bracelet for attachment to a limb of a body.

8. A transdermal device according to claim 7, wherein the unit includes an LCD and a galvanostat which regulates the current applied to the first electrode and maintains said current constant despite the varying resistance to the skin.

9. A transdermal device according to claim 1, wherein the drug substance is selected from the group consisting of clonidine, insulin, morphine, nicotine, orcipreniline, salbutamol, sodium chromoglycate and desmopressin or a pharmaceutically acceptable salt thereof.

10. A transdermal device according to claim 1, wherein said second electrode is also an electrode of the type as defined for said first electrode, such that the transdermal device incorporating said first and second electrodes may be used to administer two drugs simultaneously by the transdermal route.

11. A transdermal device according to claim 1, wherein the surface area of the first electrode adapted to be in contact with the skin is in the range of 0.1 to 30 $cm^2$.

12. A transdermal device according to claim 1, wherein the drug substance has a concentration in the range of 0.1 to 15% weight/volume based on the hydrophilic medium.

13. A transdermal device comprising a housing first electrode detachably mounted to said housing and an electrical source within said housing wherein said housing is mounted in a strap or bracelet for attachment to a limb of a body, said first electrode having a fist surface with a surface area adapted for contact with human skin when in use, a drug substance dissolved or dispersed in a hydrophilic medium defining said first electrode which can pass to the skin under the influence of an iontophoretic or electroosmotic force created by said electrical source, and a second surface remote from said first surface which is drug impermeable, electrically conducting and an integral part of said first electrode, said second surface further being adapted for contact with said electrical source, and a second electrode in said strap or bracelet for connection to said electrical source and adapted to be situated at a different site on the skin to said first electrode.

14. The transdermal device according to claim 13, wherein said second electrode is also an electrode of the type as defined for said first electrode, such that the transdermal device incorporating said first and second electrodes may be used to administer two drugs simultaneously by the transdermal route.

15. A transdermal device according to claim 13, wherein the surface area of the first electrode adapted to be in contact with the skin is in the range of 0.1 to 30 cm$^2$.

16. A transdermal device according to claim 13, wherein the drug substance has a concentration in the range of 0.1 to 15% weight/volume based on the hydrophilic medium.

* * * * *